United States Patent
Kosourov et al.

(10) Patent No.: US 7,732,174 B2
(45) Date of Patent: Jun. 8, 2010

(54) MULTI-STAGE MICROBIAL SYSTEM FOR CONTINUOUS HYDROGEN PRODUCTION

(75) Inventors: Sergey Kosourov, Pushchino (RU); Maria L. Ghirardi, Lakewood, CO (US); Michael Seibert, Lakewood, CO (US)

(73) Assignee: Alliance For Sustainable Energy, LLC, Golden, CO (US)

( * ) Notice: Subject to any disclaimer, the term of this patent is extended or adjusted under 35 U.S.C. 154(b) by 572 days.

(21) Appl. No.: 10/543,866

(22) PCT Filed: Oct. 1, 2003

(86) PCT No.: PCT/US03/30992

§ 371 (c)(1),
(2), (4) Date: Sep. 11, 2006

(87) PCT Pub. No.: WO2005/042694

PCT Pub. Date: May 12, 2005

(65) Prior Publication Data

US 2007/0269874 A1  Nov. 22, 2007

(51) Int. Cl.
*C12P 3/00* (2006.01)
*C12N 1/20* (2006.01)
*C12N 1/12* (2006.01)
(52) U.S. Cl. .................. 435/168; 435/252.1; 435/257.1
(58) Field of Classification Search .................. 435/168, 435/252.1, 257.1
See application file for complete search history.

(56) References Cited

U.S. PATENT DOCUMENTS 5,871,952 A  2/1999  Ghirardi et al.
6,277,589 B1  8/2001  Seibert et al.

OTHER PUBLICATIONS

Zhang et al., "Probing green algal hydrogen production," Phil Trans R Soc Lond B 357:1499-1509, 2002.*
Wang et al., Fermentation and Enzyme Technology, John Wiley & Sons, New York, 1979, pp. 98-108.*
Kosourov, Sergey et al., "Sustained Hydrogen Photoproduction by *Chlamydomonas reinhardtii*; Effects of Culture Parameters." Biotechnology and Bioengineering. June 2002, vol. 78, No. 7, pp. 731-740, see entire document.

* cited by examiner

*Primary Examiner*—Karen Cochrane Carlson
*Assistant Examiner*—Rosanne Kosson
(74) *Attorney, Agent, or Firm*—John C. Stolpa

(57) ABSTRACT

A method of using sequential chemostat culture vessels to provide continuous $H_2$ production, in which photosynthetic $O_2$ evolution and $H_2$ photoproduction are separated physically into two separate bioreactors, comprising: a) growing a microorganism culture able to continuously generate $H_2$ by photosynthetically producing cells at about the early-to-late log state in a first photobioreactor operating as a sulfur chemostat under aerobic and/or conditions; b) continuously feeding cells from the first photobioreactor to a second photobioreactor operating under anaerobic conditions and sulfur deprivation conditions resulting from constant uptake of sulfate in the first bioreactor and a low rate of culture flow between the first and second bioreactors, for induction of hydrogenase and $H_2$ photoproduction to allow for continuous cultivation of the microorganism's cells in the first photobioreactor and constant $H_2$ production in the second photobioreactor, and c) $H_2$ gas from the second photobioreactor.

9 Claims, 8 Drawing Sheets

MULTI-STAGE MICROBIAL SYSTEM FOR CONTINUOUS HYDROGEN PRODUCTION

CONTRACTUAL ORIGIN OF THE INVENTION

The United States Government has rights in this invention under Contract No. DE-AC3699GO10337 between the United States Department of Energy and the National Renewable Energy Laboratory, a division of the Midwest Research Institute.

BACKGROUND ART

The invention relates to a continuous $H_2$ production system in which photosynthetic $O_2$ evolution and $H_2$ photoproduction are separated physically in two separate bioreactors, wherein the first bioreactor operates as a sulfur chemostat to generate photosynthetically competent and active cells, which are continuously fed to a second photobioreactor wherein the culture produces $H_2$ under anaerobic conditions, does not accumulate toxic levels of fermentation products, and is continuously replenished by fresh cells from the first chemostat to prevent complete inactivation of $H_2$-production activity and claims benefit of the Oct. 1, 2002 filing date of provisional application P60/414,993.

TECHNICAL FIELD

Many classes of microorganisms are able to produce $H_2$. Among them are some anaerobic and photosynthetic bacteria, cyanobacteria, and green algae.

However, sustained algal $H_2$ photoproduction can only occur if $O_2$, a co-product of photosynthesis, is continuously removed from the medium by the addition of reductants or $O_2$ scavengers, or purging with neutral gases, all costly propositions. This is necessary due to the sensitivity of the algal hydrogenase enzyme to $O_2$. Two possible ways to circumvent the $O_2$-inhibition problem in algae are currently being pursued. In the first, molecular biology approaches are being used to engineer an $O_2$-tolerant hydrogenase that functions under aerobic conditions. The second approach consists of separating the $O_2$-evolution and $H_2$-production activities temporally in the cultures.

Sustained algal $H_2$ photoproduction for up to 4 days is currently attained in batch cultures, where the algal cells transition from a photosynthetic, $O_2$-evolution phase to an anaerobic, $H_2$-production phase. The transition is achieved by depriving the cultures of sulfate. This is done by rigorously washing the cells 1-5 times in minus-sulfur medium, and then re-suspending them in the same medium. Under sulfur-deprived conditions, photosynthetic $O_2$-evolution activity is partially (but reversibly) inhibited, and the cultures become anaerobic due to the continuous respiration of accumulated starch and/or other endogenous substrates. Anaerobiosis is necessary and sufficient to induce the synthesis of a reversible hydrogenase enzyme, which catalyses $H_2$ production, using reductants originated mostly, but not entirely, from residual photosynthetic-water splitting function. In the batch mode, $H_2$ photoproduction is transient, lasting from 3-4 days, since sulfur deprivation eventually affects all other cellular activities (besides photosynthetic $O_2$ evolution). However, algal cultures can be rejuvenated, at that point, by re-adding sulfate to the medium for a 2-day period.

At the present, the batch sulfur-deprived algal system is not commercially viable due to its high cost. Some of the reasons for this are:

a) the low specific rates of $H_2$ photoproduction;

b) the short period of time during which cultures actually produce $H_2$; and c) the expensive centrifugation step required to deprive the culture of sulfate.

In T. V. Laurinavichene et al. Different Methods To Deprive *Chlamydomonas reinhardtii* Cultures Of Sulfur For Subsequent Hydrogen Photoproduction. *J. Int. Hydrog. Energy, in press*. (2002), it is demonstrated that it is possible to deprive the cultures of sulfate without relying on centrifugation.

Kosourov et al. in Sustained Hydrogen Photoproduction By *Chlamydomonas reinhardtii*: Effects of culture parameters. Biotechnol Bioeng 78: 731-740. (2002), disclose that the re-addition of small amounts of sulfate to the cultures at the start of sulfur-deprivation resulted in higher specific rates and yields of $H_2$ photoproduction.

SUMMARY

One object of the present invention is to provide a continuous $H_2$-production system based on the effects of sulfur-deprivation on algal photosynthesis and physical separation of the net $O_2$ and $H_2$ production processes in algal cultures.

Another object of the present invention is to provide a continuous $H_2$-production system based on the effects of sulfur deprivation on algal photosynthesis and physical separation of the net $O_2$ and $H_2$ production, wherein the yield of the continuous system is comparable or better than that of the batch system with substantially lower cost due to the elimination of many centrifugation steps.

A further object of the present invention is to provide a continuous $H_2$-production system based on the effects of sulfur-deprivation on algal photosynthesis and physical separation of the net $O_2$ and $H_2$ production, wherein the algal $H_2$ production is stable for at least 14 days and is maintained at a stable rate of about 4.7 μmols $H_2 \cdot mg\ Chl^{-1} \cdot h^{-1}$.

In general, the invention is accomplished by:

a) starting the two-bioreactor system and initiating hydrogen photoproduction in the second vessel without centrifuging;

b) running both vessels under conditions where just enough healthy cells are continuously delivered to the second vessel to support maximal hydrogen production;

c) circulating fluids to recycle as much liquid as possible;

d) obtaining valuable by-products by removing and recovering cells from the second vessel and separating compounds from the spent medium;

e) removing build-up materials in the return fluid that negatively affect cell growth in the first vessel and subsequent $H_2$ production in the second vessel;

f) recycling acetate produced in the second vessel back to the first vessel where acetate is required to produce cells capable of evolving hydrogen in the second vessel;

g) transferring cells from the first to the second vessel in a manner that does not carry over oxygen; and h) delivering the cells to the second vessel in a state that allows them to immediately produce hydrogen without the delay normally present in current processes.

DETAILED DESCRIPTION OF THE INVENTION

Materials and Methods

Cell Growth Conditions

Wild type *Chlamydomonas reinhardtii*, strain cc124 (mf), was pre-grown photoheterotrophically in batch cultures on a standard Tris-Acetate-Phosphate (TAP) medium in 1-L Erlenmeyer flasks at about 25° C.; however, other $H_2$-producing, oxygenic photosynthetic organisms can also be used.

The culture volume was about 800 mL, and algal cultures were bubbled with air containing 2% $CO_2$. The gas mixture was sterilized using membrane filters with a 0.2 µM pore size (Acro 37 TF, Gelman Sciences, Inc., Ann Arbor, Mich.). During growth, algae were continuously illuminated with cool-white fluorescent light of about 200 µE·m$^{-2}$·s$^{-1}$ PAR and mixed by magnetic stirring (PC-131, Corning Inc., NY). After reaching the late logarithmic phase (4-6×10$^6$ cells·mL$^{-1}$), cells were harvested by centrifugation at 3000×g for 5 minutes. Harvested cells were washed once in TAP-minus-sulfur medium and resuspended in a small volume of the same medium. The cultures could also have been grown under limiting sulfate conditions to eliminate the washing step. This culture material was used to inoculate two bioreactors: the first bioreactor for chemostatic culture growth and the second for $H_2$ photoproduction.

TAP-minus-sulfur medium was modified from a standard TAP medium by replacing all sulfates with chloride salts at the same concentrations. All procedures with algal cultures mentioned above (i.e. washing and transfer from one flask to another) were performed under sterile conditions.

Continuous Flow Photobioreactor System

Figure 1:
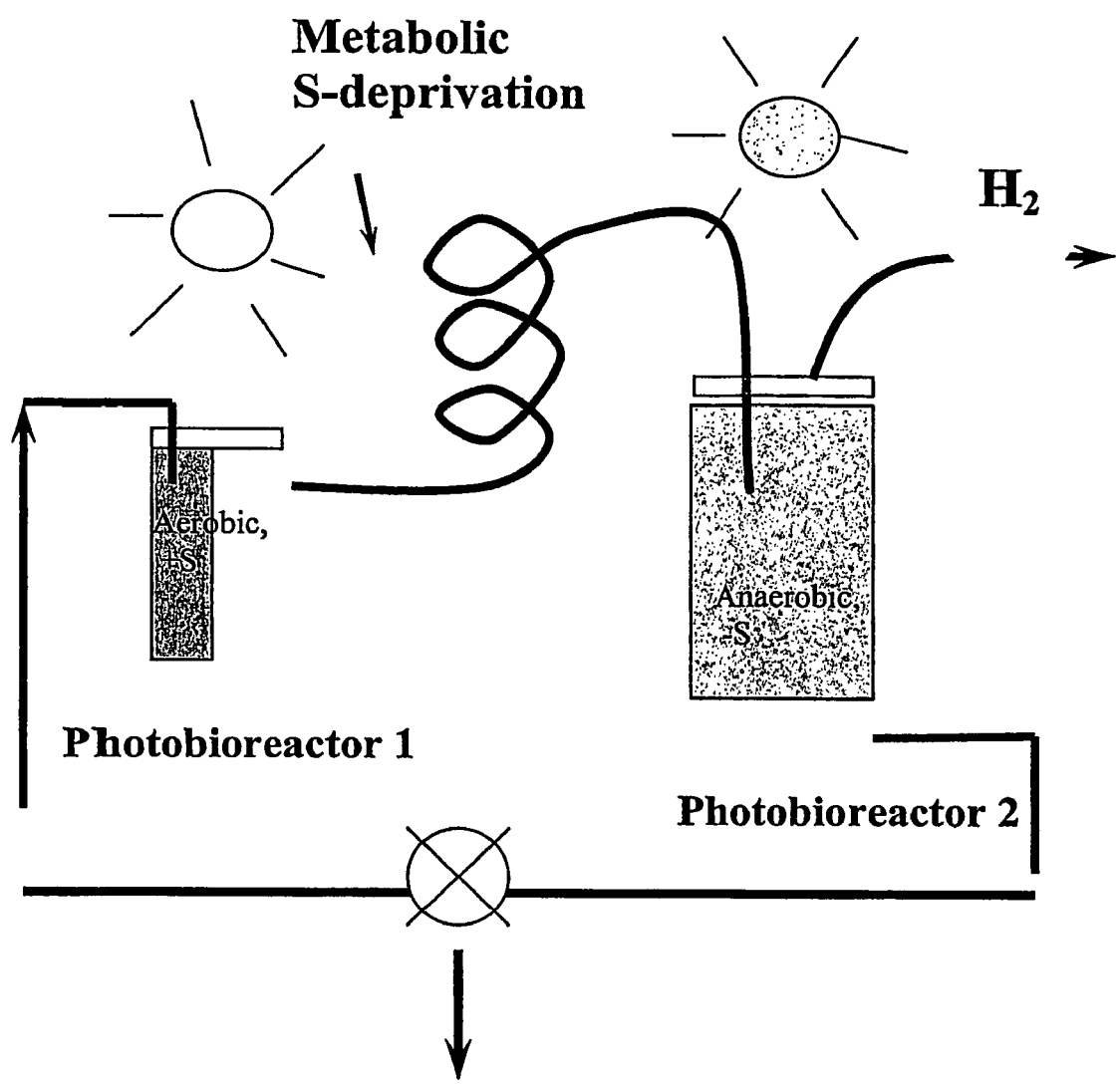
FIG. 1 is a drawing depicting the concept of the two-bioreactor, continuous flow system for algal $H_2$ production of the invention.

FIG. 1 is a drawing showing the concept for the two reactor, continuous flow system for algal $H_2$ production.

Figure 2:
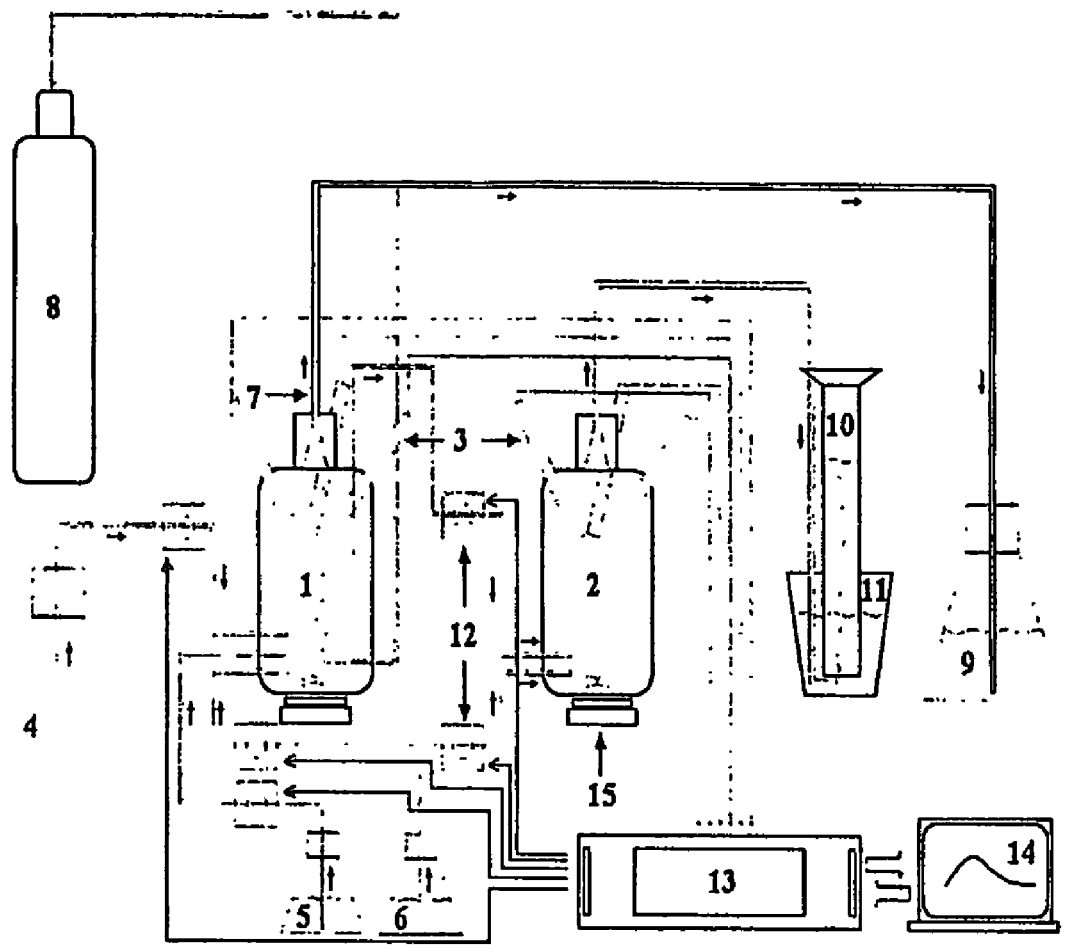
FIG. 2 is an example of a schematic of the computerized photobioreactor system of the invention for continuous cultivation of algae under sulfur-limiting conditions and for $H_2$ photoproduction.

A schematic of the computerized photobioreactor system designed for continuous cultivation of algae under sulfur-limiting conditions and for $H_2$ photoproduction is shown in FIG. 2. The system employs two (1, 2) specially fabricated, glass photobioreactors (4-cm optical path length, 1.1-L culture volume) with built-in ports (3) for dissolved $O_2$ (p$O_2$), redox ($E_h$) and pH plus temperature (pH-T) sensors. Each photobioreactor has three inlets for fresh medium (4) and titrants (5—base, 6—acid) and one outlet for gas and cell suspension (7).

The first photobioreactor has an additional inlet for bubbling the algal culture with a sterile $CO_2$/air gas mixture (8). Excess cell suspension in the first bioreactor, if any, together with any produced gas are disposed of into a collector flask (9). Alternatively, at the example dilution rates used in this example, the excess material could be used to supply a second $H_2$-producing photobioreactor. The first photobioreactor (1) supplies the second photobioreactor (2) with the cell biomass and sulfate-depleted medium (12, top arrow).

The gas produced by the second bioreactor is collected in an upside-down graduated cylinder filled with water (10). At the same time, excess cell suspension from the second bioreactor is disposed of in a second collector flask (11). In a commercial system, this material would be recycled back to the first photobioreactor. The flow of all liquids in the system is maintained by pumping through Tygon LFL tubing (0.89 mm i.d., 96429-26, Cole-Parmer Instrument Co, Illinois) with six peristaltic pumps (12) (MasterFlex C/L 77120-70, Cole-Parmer Instrument Co, Illinois) operating under the control of a microprocessor system. Finally, the microprocessor system (13, 14), consisting of two computers, is used for data storage and processing. The first computer (13), consisting of four PCA-6135/L microprocessor motherboards and an IPC-620 chassis (Advantech, Sunnyvale, Calif.) processes and stores the data obtained by the sensors, controls the dilution rates in both photobioreactors independently, and holds the pHs inside bioreactors at a given value. The second computer (14) (a P-II, 400 MHz, Toshiba notebook) is used for calibrating the sensors, changing the operating parameters, and on-line monitoring of the growth conditions inside the photobioreactors. Both computers communicate via the RS-232 port.

Figure 3:
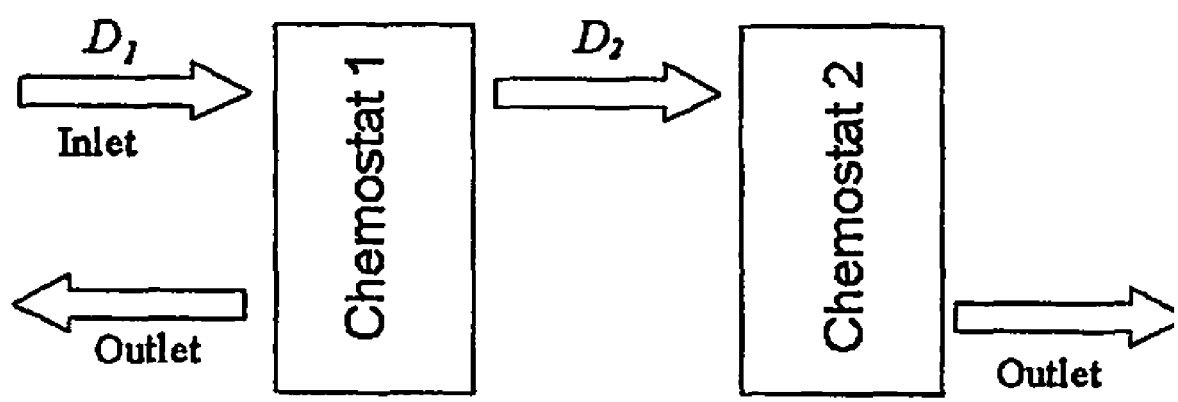
FIG. 3 is a schematic showing the principles of operation of the double chemostat system of the invention, inclusive of D1 and D2 dilution rates for photobioreactor 1 (PhBR1) and photobioreactor 2 (PhBR2).

PhBR1 operates as a classical chemostat under sulfate-limiting conditions and supplies PhBR2 with the healthy cell biomass (FIG. 3). The cell density in the first bioreactor will depend on the sulfate level in the medium and the dilution rate, $D_1$. The purpose of PhBR2 is to produce $H_2$ continuously. The algal cells in this bioreactor experience severe sulfur-deprivation conditions due to the constant uptake of sulfate in the first bioreactor by the growing culture, and due to the lower rate of culture flow between the two bioreactors, $D_2$ (where $D_1 > D_2$). Under severe sulfur deprivation, algal cells partially inactivate their $O_2$-evolving activity and, as a result, make their environment anaerobic enough to allow $H_2$ to be produced. The establishment of such an anaerobic environment inside the second photobioreactor is necessary for induction of the hydrogenase and, hence, for $H_2$ photoproduction. The algal culture does not grow under these conditions. The cell density in the second photobioreactor will depend on the cell density in the first bioreactor, the rate of culture flow between the two bioreactors and out of PhBR2 ($D_2$), and the rate of cell death under sulfur deprivation. The system in this configuration allows for the continuous cultivation of healthy algal cells in PhBR1 and constant $H_2$ production in PhBR2.

Procedures

The experiment begins with a period of pre-cultivation of the algal culture in the first photobioreactor under sulfur-limiting conditions. For this, PhBR1, containing 900-1000 mL of TAP-minus-sulfur medium with 75 µM sulfate, was inoculated with 100-200 ml of *Chlamydomonas reinhardtii* culture to a final chlorophyll concentration of about 5-10 µg/mL. The inoculum used was prepared as described above (see "Cell Growth Conditions" Section). The photobioreactor was placed under two-sided illumination of ~200-220 µE·m$^{-2}$·s$^{-1}$ PAR (eight 40-W cool-white fluorescence lamps), connected to input and output tubing and cultivation was started by adjusting the dilution rate to 0.04 h$^{-1}$ (D1). The bioreactor was fed with TAP-minus-sulfur medium containing 75 µM of sulfate. The algal culture inside the photobioreactor was mixed by magnetic stirring and bubbled with 3% $CO_2$ in air. The gas mixture was sterilized by passing it through membrane filters. Once the culture in the first bioreactor was close to steady-state, cultivation of algal cells in PhBR2 was started. The photobioreactor was filled with 1.1 L of cell suspension in TAP-minus-sulfur medium and placed under the same light and mixing conditions as the first photobioreactor.

The algae in the second bioreactor were cultivated initially in the batch mode. When the algal culture in this bioreactor began producing $H_2$, PhBR2 was connected to PhBR1 and the liquid flow between the two bioreactors was adjusted to a dilution rate of 0.02 h$^{-1}$ (D2). Under our example conditions, the transit time for the culture to travel from PHBR1 to PhBR2 was 0.3 min. In this mode, the photobioreactor system was operated for a prolonged period (up to 14 days). The pHs in both bioreactors were kept constant by automated addition of 0.2 M NaOH or 0.2 M acetic acid at, respectively, 7.5 and 7.8.

Flash-Probe Chl a Fluorescence

The fluorescence yield of Chl a following a saturating single-turnover light flash reflects changes in the level of $Q_A^-$, the reduced form of the primary stable electron acceptor in PSII. The amount of $Q_A^-$, generated under our experimental conditions, is a measure of the photochemical capacity of PSII in the cultures and is related to $F_{max}$ (see below). Flash-induced Chl a fluorescence yields were measured with a home-built instrument. Samples used for fluorescence measurements were taken directly from each PhBR, concentrated by a centrifugation to get a total chlorophyll concentration of 40±1 µg/ml and adapted in the dark for 5 minutes under atmospheric $O_2$ partial pressure. The samples were placed in a 4 mm×10 mm plastic cuvette, and DCMU was added to a final concentration of 30 µM to block an electron transfer between $Q_A^-$ and $Q_B$ (the secondary electron acceptor) on the reducing side of photosystem II. Fluorescence was initiated by a saturating actinic flash and the corresponding fluorescence yield was measured as $(F-F_0)/F_0$. The initial maximum fluorescence level, $F_{max}$, appears within 20-40 µs following the saturating flash and decays to a low final level, $F_{final}$ within 3 s.

The chlorophyll a+b content was assayed spectrophotometrically in 95% ethanol extracts by the method of Spreitzer (Harris, 1989).[1] The cell density was measured indirectly by the absorbance of the cell suspension at 750 nm and related to the corresponding chlorophyll concentration.

[1] E. H. Harris The *Chlamydomonas* sourcebook: a comprehensive guide to biology and laboratory use. Academic Press, San Diego (1989).

Results

As observed, it is possible to deprive algal cells of sulfate without using costly centrifugation. This can be done by diluting sulfur-replete cultures either in sulfur-minus medium or in sulfur-limiting medium. In the experiments described here, however, we utilized centrifugation to carefully wash out sulfate and re-suspended the cultures in medium of defined sulfate concentration (75 µM in PhBR1), in order to better examine the experimental parameters.

Figure 4:
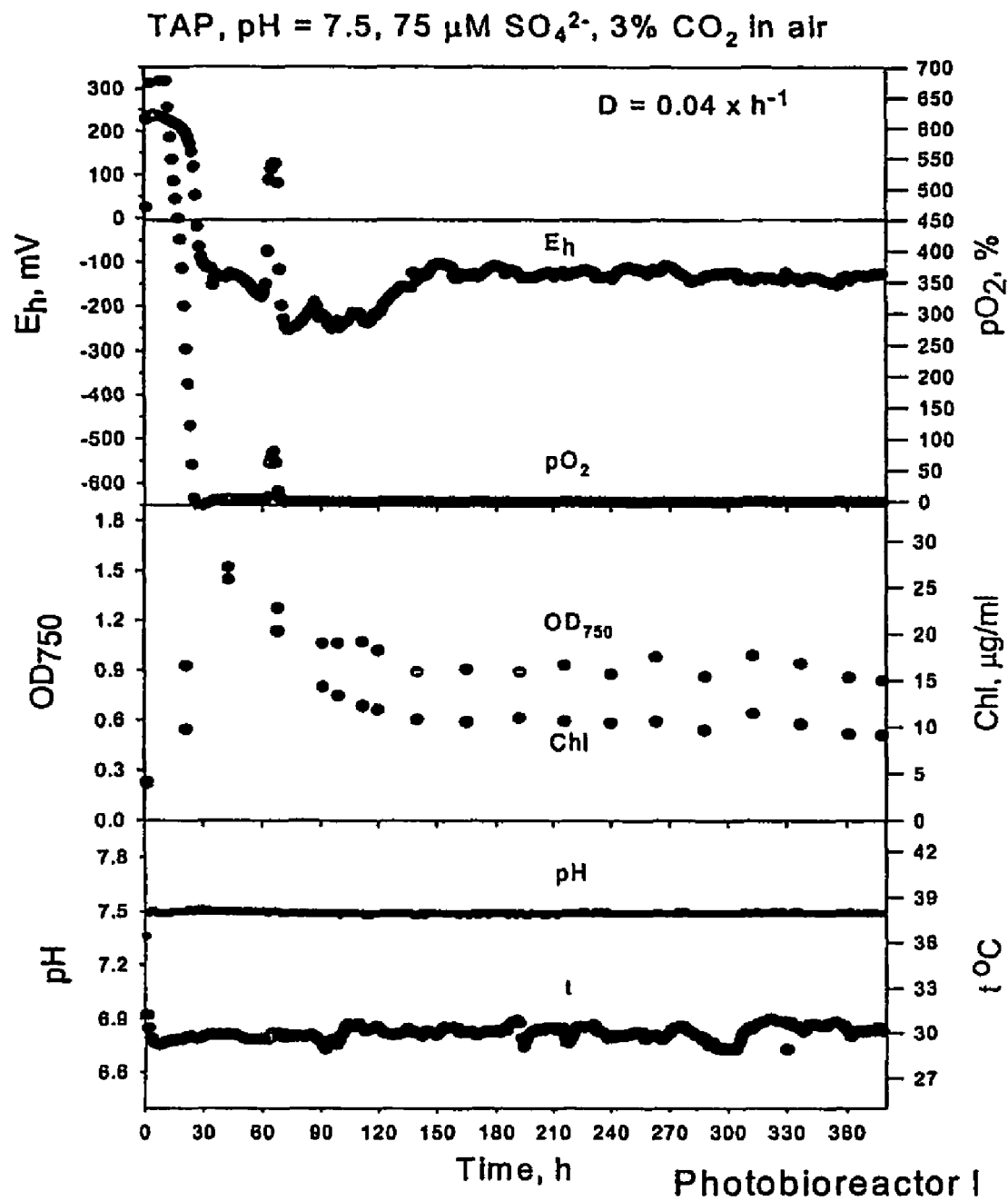
FIG. 4 is a graph showing biophysical and biochemical parameters associated with establishment of steady-state growth in PhBR1 under continuous dilution with TAP buffer containing 75 µM of sulfate.

The algal cultures in the first photobioreactor were grown chemostatically under constant dilution with medium containing 75 µM sulfate, at a rate of 0.04 h$^{-1}$. These conditions resulted in a rapid transition of the culture to an anaerobic environment (where the rate of photosynthetic $O_2$ evolution~rate of respiratory $O_2$ consumption in the cells), as monitored by changes in redox potential and dissolved $O_2$ content of the culture medium (FIG. 4, $pO_2$ and $E_h$). The redox potential of the medium decreased to about −250 mV (measured against an Ag/AgCl reference electrode) and then equilibrated at about −150 mV. No dissolved $O_2$ was detected in solution during the rest of the incubation period. The pH of the culture was kept constant at 7.5 by automatically titrating in 0.2 M acetic acid and 0.2M NaOH. That pH value has been shown to be optimal for photosynthetic growth of the cells. After the transition to anaerobiosis, the growth rate of the algal culture decreased and eventually reached a steady-state level (FIG. 4, $OD_{750}$ and Chl), at a stable chlorophyll concentration of about 10 µg/mL. When the cultures reached steady state, at t=113 h, they were pumped into the second photobioreactor at a constant dilution rate of 0.02 h$^{-1}$.

Figure 5:
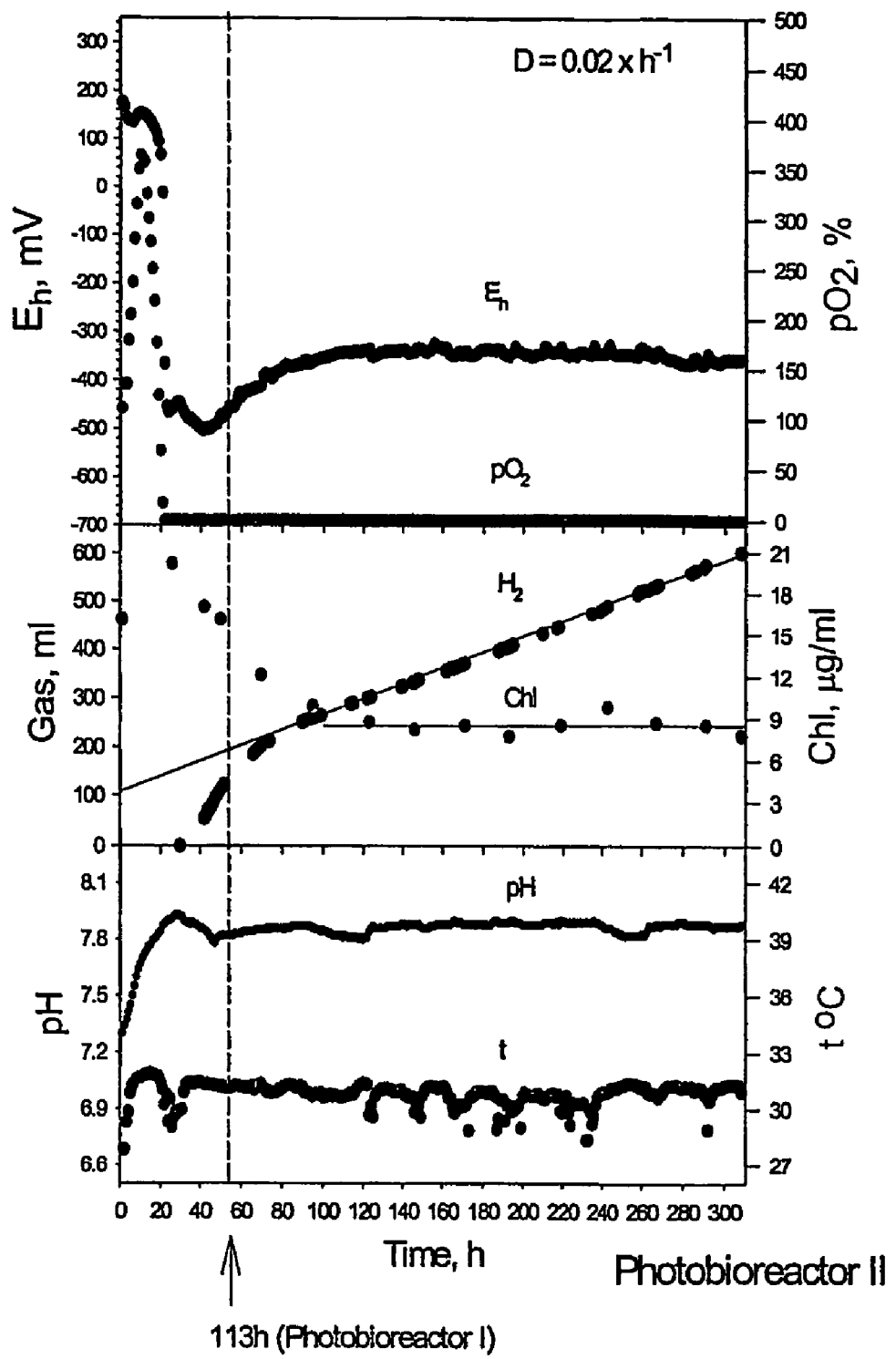
FIG. 5 is a graph showing biophysical and biochemical parameters measured in PhBR2. The experiment was started in the batch mode. The chemostat mode began at the time indicated by the arrow, as cells from PhBR1 were used to replace those in PhBR2.
Figure 6:
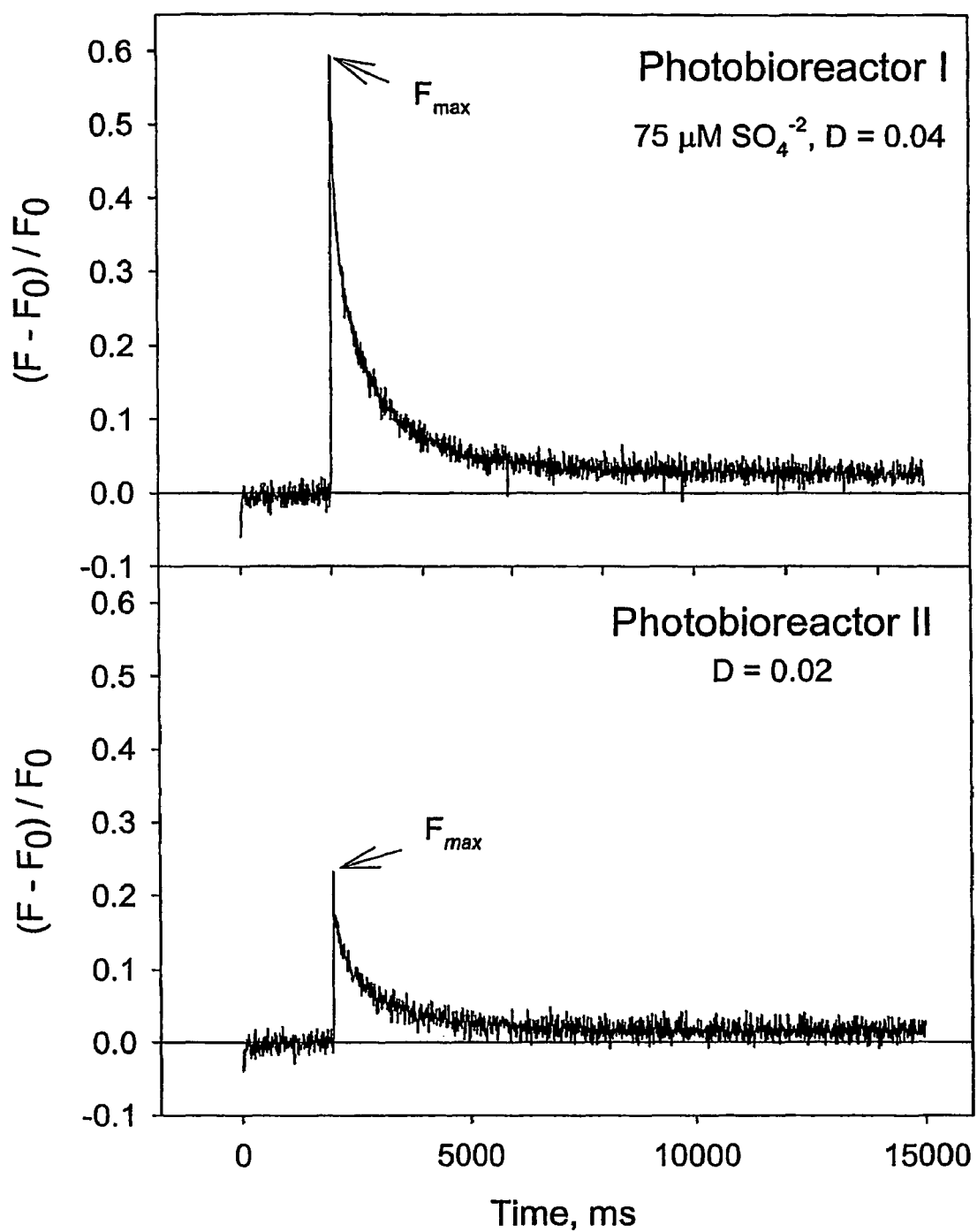
FIG. 6 is a graph showing single turnover, flash-induced fluorescence yields of samples taken from the two photobioreactors after steady-state growth is established. The highest fluorescence yield, $F_{max}$, is a measure of the PSII capacity of the cultures.

The second photobioreactor was started in the batch mode. As seen in FIG. 5, under complete sulfur deprivation, the algal culture quickly becomes anaerobic. The redox potential ($E_h$) reached a significantly more negative value (−450 to −500 mV) as compared to PhBR1 (where the steady-state $E_h$~−100-mV and no significant $H_2$ production was observed), and then climbed steadily to about −350 mV after $H_2$ production started. After 24 h of $H_2$ photoproduction in PhBR2, the flow of fresh cells from the first photobioreactor was initiated. In our system, tubing with a total volume of 1 ml connects the two photobioreactors, delivering cells from PhBR1 to PhBR2 in about 0.3 minutes. The chlorophyll concentration reached steady-state (about 8-9 µg/mL) at t=100 h, and the pH of the medium was kept at 7.8 by titration with 0.2 M NaOH. After an initial decrease in the $H_2$-production rate, the culture in the second bioreactor reached a steady-state rate of $H_2$ production of 4.7 µmoles/(mg Chl·h), compared to 12.1 µmoles/(mg Chl·h) initial rates in the batch mode. The former rate was sustainable for the remainder of the experiment (another 220 h, and 600 ml of $H_2$ gas was produced. The $E_h$ in PhBR2 did not decrease below the steady-state level after 2 days of $H_2$ production. A decrease in $E_h$ is characteristic of decreased $H_2$-production rates and cell death in batch cultures (data not shown). Upon optimization, both higher $H_2$ production rates and longer durations of $H_2$ production can be expected. This will involve adjusting the dilution rates, sulfate concentration in PhBR1, and transfer times between PhBR1 and PhBR2. The photosynthetic capacity of the cultures in both reactors was assessed by means of flash-induced fluorescence yield measurements. FIG. 6 shows that the photosynthetic photochemical capacity of the cultures in PHBR1 ($F_{max}$=0.6), measured after steady-state conditions were established, is equal to that of algal cultures grown under fully aerobic, sulfur-replete, photosynthetic conditions. Moreover, the culture in PhBR2 maintains photosynthetic activity at a value ($F_{max}$=0.2) that corresponds to or is slightly lower than the level measured in the batch culture during the period of peak $H_2$ production.

To improve our current batch algal $H_2$-production system, we devised a process based on two sequential chemostats where (a) centrifugation of the cultures to deprive them of sulfate after start-up was eliminated, (b) fresh, photosynthetically-competent cells (PhBR1) continuously replace dying, $H_2$-producing organisms (PhBR2), (c) circulating fluids can be recycled, (d) valuable co-products can be generated, (e) the accumulation of inhibitors of growth and/or $H_2$ production is prevented, (f) acetate, required for rapid decrease of the $O_2$-production function and subsequent anaerobiosis in PhBR2, can be recycled, (g) oxygen is eliminated by continuous respiratory activity of the cells, and (h) the cells delivered to the $H_2$-producing reactor maintain the culture producing $H_2$ continuously.

The first reduction to practice led to two important observations. The first was that the continuous addition of 75 µM sulfate to the first chemostat under our dilution rates resulted in a steady-state Chl concentration and no detectable $O_2$ in PhBR1, and a continuous $H_2$ photoproduction in PhBR2. This was surprising since a one-time addition of even 1 µM sulfate directly to a $H_2$-producing bioreactor during the $H_2$-production phase in batch cultures is known to significantly inhibit $H_2$ production. In our concept of a continuous system, we thought that aerobiosis in the culture would be required to maintain the cells photosynthetically active in PhBR1. This prediction was based on experiments in our lab, showing that $O_2$-evolution capacity of algal cells is inactivated by incubation under dark, anaerobic conditions even in the presence of sulfate. However, as seen in FIG. 6, the photosynthetic capacity of PSII is very high in PhBR1, comparable to that of photoheterotrophically-grown cells at normal sulfate concentrations. We also tried other limiting sulfate concentrations in PHBR1 at the previous dilution rates, with negative results. Below 50 µM sulfate, the culture in PHBR1 reached a much lower steady-state Chl concentration, and was not able to maintain high rates of $H_2$ production by PhBR2. At 90 µM sulfate or above, the steady-state redox potential in PhBR1 was too high and the transport of the culture to PhBR2 actually inhibited $H_2$ production. Transit times between PHBR1 and PhBR2 of >> 0.3 min. may be necessary at these higher sulfate concentrations in PHBR1 to maintain $H_2$ production in PhBR2.

It is important to note that the steady-state Chl concentration in the first chemostat depends both on the amount of sulfate with which it is continuously diluted and on the dilution rate utilized. Initial experiments at dilution rates of 0.02, 0.03 and 0.04 $h^{-1}$ led to the choice of the latter, but this was done at 75 µM sulfate, and this example may not be optimal yet from the process perspective. Additionally, the optimal sulfate concentration in PhBR1 to support $H_2$ production by the cultures in PhBR2 will vary depending on the time that it takes to deliver the cells to PhBR2, a factor that will determine the overall activity of the delivered cells.

Figure 7:
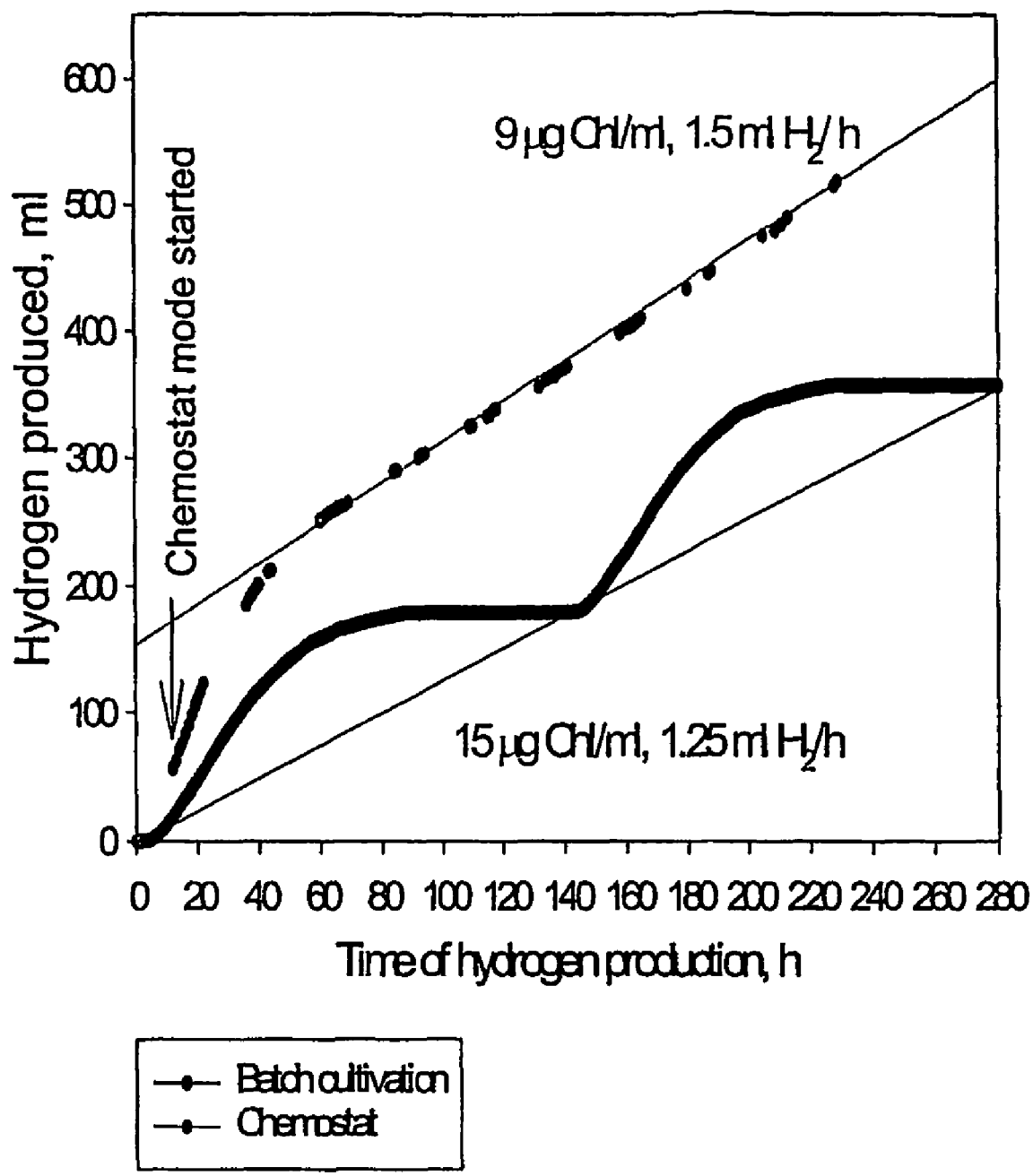
FIG. 7 is a graph showing comparison between the rates of $H_2$ production by cells grown under batch and continuous (chemostat) modes.

The second important observation resulting from our experiments is that the total yield of $H_2$ using the continuous system is higher than the corresponding average amount using the batch system, as shown in FIG. 7. We point out that the results for the batch system in FIG. 7 includes a 2-day "down period" used to rejuvenate the culture. This is done by adding sulfate back to the cultures, allowing photosynthetic $O_2$ evolution activity to recover, and submitting the cultures to a second round of sulfur deprivation by centrifugation. The yield of the continuous system compares quite favorably with the corresponding yield of the batch system, without the accompanying disadvantages of the latter's high cost of operation. Moreover, the total $H_2$ yield from the continuous system is actually double that shown in FIG. 7, because, under the described operating procedures ($D_1=2\times D_2$, FIG. 2), each PhBR1 can be used to run two PhBR2s. As can be seen, specific rates of $H_2$ production over the time of the experiments are:

4.7 µmoles $H_2$/(mg Chl×h)—continuous mode;
3 µmoles $H_2$/(mg Chl×h)—batch mode.

Figure 8:
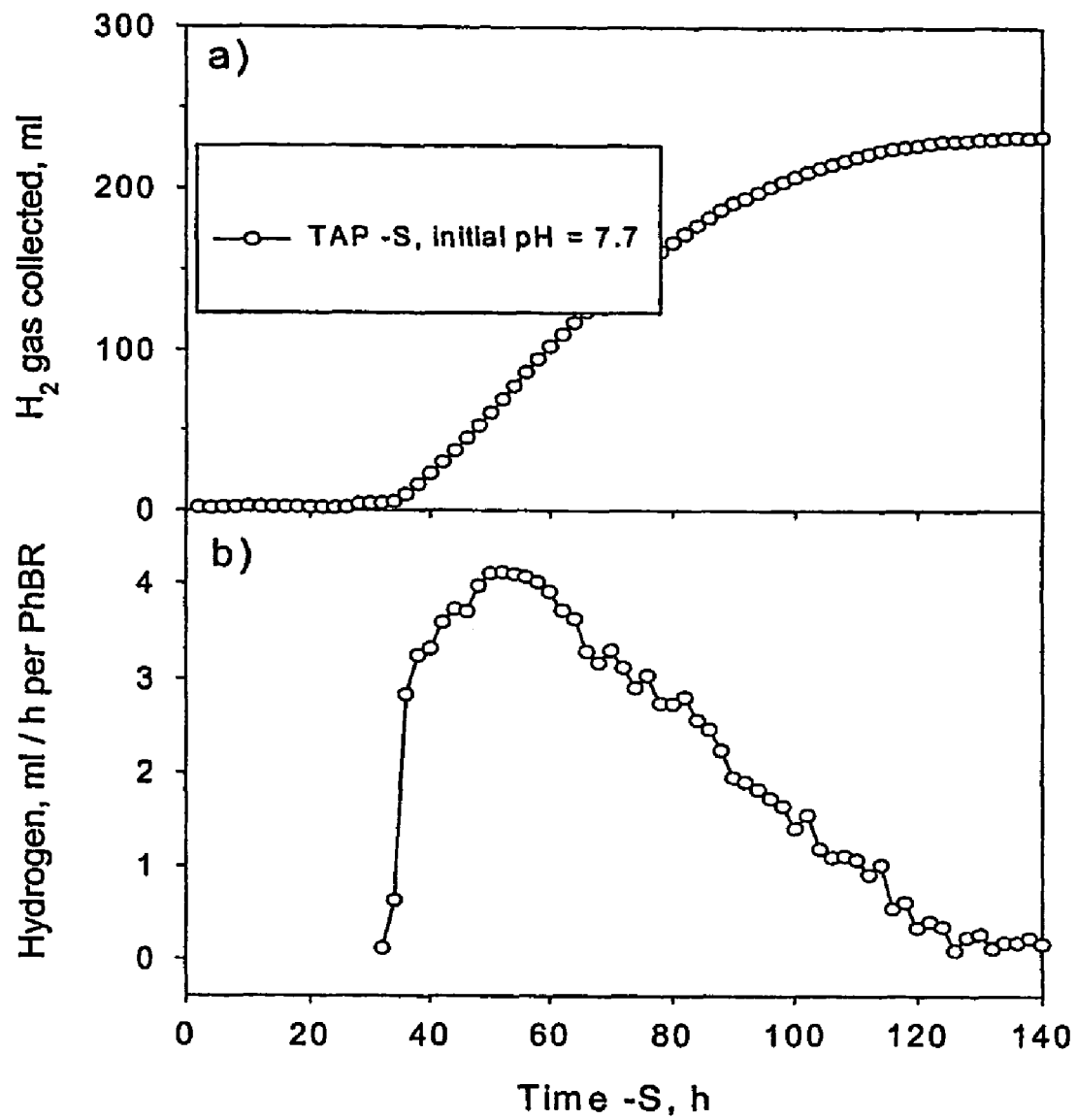
FIG. 8 is a graph showing the amount of $H_2$ gas collected and changes in the rate of $H_2$ gas collected and changes in the rate of $H_2$ photoproduction during the sulfur-deprivation process in the batch mode. The maximal rate of $H_2$ production is equivalent to 9.4 µmoles $H_2$/(mg/Chl$^{-1}$×h$^{-1}$), but this is not sustainable.

Even though the current rate of continuous $H_2$ photoproduction is high, our aim is to achieve the highest possible rate. This target is shown in FIG. 8, where the rate of $H_2$ photoproduction is plotted as a function of time under sulfur deprivation in a medium of pH=7.7 using A TYPICAL "batch culture" experiment. The rates initially increase, as the medium becomes anaerobic, reach a maximum value, and promptly decrease under the batch growth conditions. At its peak, this culture produced $H_2$ at 4 ml/h (or 9.4 µmoles·mg $Chl^{-1} \cdot h^{-1}$), which represents close to the upper limit for the reaction under these particular experimental conditions. These maximum specific rates are about twice as high as that of the continuous system and represent our goal for $H_2$-production rates in the latter.

In summarization, we have developed a continuous $H_2$-production system based on the effects of sulfur-deprivation on algal photosynthesis and physical separation of net $O_2$ and $H_2$ production in the cultures. The yield of the continuous system is comparable to or better than that of the batch system with substantially lower cost due to the elimination of many centrifugation steps. Algal $H_2$ production was shown to be stable for at least 14 days and to be maintained at a stable rate of about 4.7 µmoles $H_2$·mg $Chl^{-1} \cdot h^{-1}$.

We claim:

1. A method of using sequential chemostat culture vessels to provide continuous $H_2$ production, in which photosynthetic $O_2$ evolution and $H_2$ photoproduction are separated physically into two connected bioreactors, comprising;
    a) growing a microorganism culture able to continuously generate $H_2$ by photosynthetically producing cells at about the early-to-late log state in a first photobioreactor operating as a sulfur chemostat under aerobic and/or anaerobic conditions;
    b) continuously feeding cells from the first photobioreactor to a second photobioreactor operating under anaerobic conditions and sulfur deprivation conditions to induce hydrogenase and $H_2$ photoproduction to provide continuous cultivation of said microorganism's cells in the first photobioreactor and constant $H_2$ production at a stable rate in the second photobioreactor; and
    c) collecting the $H_2$ gas from the second photobioreactor.

2. The method of clam 1 wherein said microorganism is selected from the group consisting of photosynthetic bacteria, cyanobacteria, and green algae.

3. The method of claim 2 wherein said green algae is *Chiamydomonas reinhardtii*.

4. The method of claim 3 wherein in step a) said *Chiamydomonas reinhardtii* is grown under fluorescence illumination.

5. The method of claim 4 wherein subsequent to fluorescence illumination said first photobioreactor is supplied with a continuous addition of a Iris-Acetate-Phosphate (TAP)-sulfur medium containing an amount of sulfate, at a rate sufficient to provide an anaerobic environment.

6. The method of claim 5 wherein, in said anaerobic environment in the first photobioreactor, the rate of photosynthetic $O_2$ evolution is equal to the approximate rate of respiratory $O_2$ consumption in cells of said *Chiamydomonas reinhardtii*.

7. The method of claim 6 wherein, between steps a) and b) continuous feeding of cells produced in said first photobioreactor into said second photobioreactor is commenced after $H_2$ photoproduction has started in said second reactor.

8. The method of claim 7 wherein, said amount of sulfate, at a rate sufficient to provide an anaerobic environment provides a steady-state chlorophyll (Chl) concentration, no detectable $O_2$ in said first photobioreactor, and a continuous $H_2$ photoproduction in said second photobioreactor.

9. The method of claim 1, wherein $H_2$ is continuously produced in the second photobioreactor for at least 14 days.

* * * * *